United States Patent [19]
Otto

[11] Patent Number: 5,769,823
[45] Date of Patent: Jun. 23, 1998

[54] IMPLANTABLE INFUSION PUMP

[75] Inventor: Karl-Heinz Otto, Kiel, Germany

[73] Assignee: Tricumed GmbH, Kiel, Germany

[21] Appl. No.: 737,842

[22] PCT Filed: Mar. 22, 1995

[86] PCT No.: PCT/DE96/00496

§ 371 Date: Nov. 25, 1996

§ 102(e) Date: Nov. 25, 1996

[87] PCT Pub. No.: WO96/29105

PCT Pub. Date: Sep. 26, 1996

[30] Foreign Application Priority Data

Mar. 23, 1995 [DE] Germany ............ 195 10 583.4

[51] Int. Cl.⁶ .................................................. A61M 31/00
[52] U.S. Cl. ................................ 604/141; 604/140
[58] Field of Search ............................. 604/131, 140, 604/141, 146

[56] References Cited

U.S. PATENT DOCUMENTS

| | | | |
|---|---|---|---|
| 3,731,681 | 5/1973 | Blackshear et al. | 604/141 |
| 4,237,881 | 12/1980 | Beigler et al. | 604/141 |
| 4,468,220 | 8/1984 | Willbanks | 604/140 |
| 4,564,363 | 1/1986 | Bagnall et al. | 604/140 X |
| 5,067,943 | 11/1991 | Burke | 604/141 |
| 5,318,540 | 6/1994 | Athayde et al. | 604/141 |
| 5,382,236 | 1/1995 | Otto et al. | 604/141 |

*Primary Examiner*—Sam Rimell

[57] ABSTRACT

Implantable infusion pump having a casing, which receives a bellows receiving a propellant producing a vapour pressure and forming a space receiving a medicament and having a throttle means and a connection for a catheter, in which the space receives at least one resilient plastic bag containing the medicament and which is provided with a coupling piece to be attached to the throttle means.

6 Claims, 1 Drawing Sheet

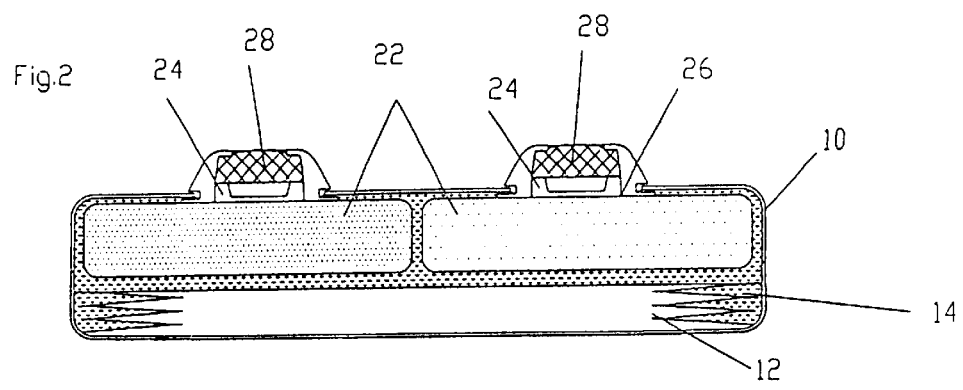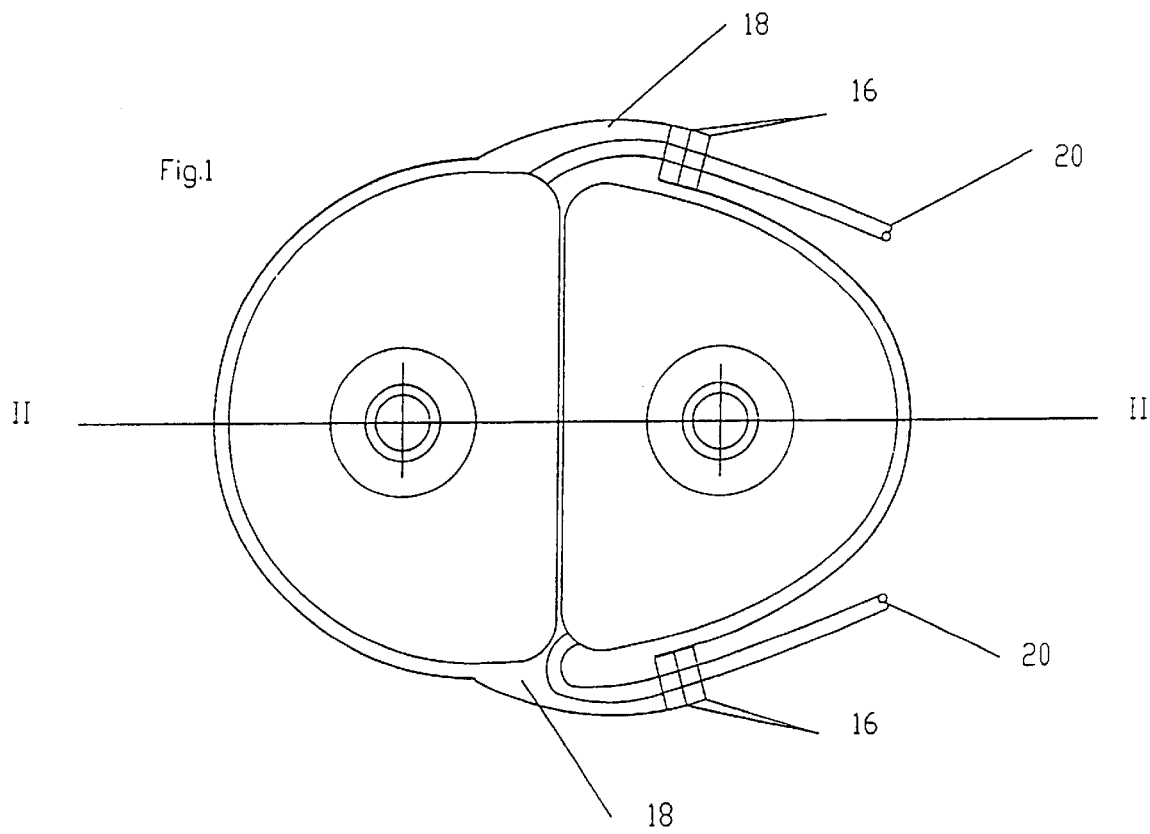

IMPLANTABLE INFUSION PUMP

The invention relates to an implantable infusion pump having the features of the preamble of claim 1 and such as is e.g. known from DE 26 04 113 C2. U.S. Pat. No. 4,820,273 discloses an infusion pump, in which a membrane referred to as a bladder defines a medicament area with respect to a pressure area.

The infusion pumps according to the preamble are implanted in patients having a constant need for a medicament supply, e.g. patients in pain and spastics.

The known infusion pumps have a very complicated manufacture. The casing is regularly made from titanium, which is laser-welded for bringing about a seal. The cleanness and sterility requirements with respect to the casing interior are extremely high. Therefore the manufacture of such infusion pumps is very expensive.

The problem of the invention is to provide an inexpensively manufacturable infusion pump.

According to the invention this problem is solved by the features of claim 1. The subclaims give advantageous developments of the invention.

The invention is described in greater detail hereinafter relative to the drawings, wherein show:

FIG. 1 A plan view of such an infusion pump.

FIG. 2 A sectional view along line II—II of FIG. 1.

The infusion pump has a plastic casing 10, which receives a bellows 12, which in turn receives a propellant producing a vapour pressure. In the represented embodiment, the remaining space 14 receives two resilient plastic bags 22, which in each case contain a medicament. The part of the space 14 not occupied by the bags 22 is filled with a liquid, e.g. glycerin, which does not attack the material of the bag and the casing. The liquid is chosen in such a way that it chemically binds the propellant passing out of the bellows 14, so that it cannot penetrate through the plastic casing into the body of the patient.

The casing 10 also carries a throttle means 16, to which is connected a connection for a catheter 20.

The upper surface of the casing 10 directed towards the skin of the patient after implanting the infusion pump is provided with a number of recesses 26 corresponding to the number of bags 22 to be received. Said recesses receive a plug 18 placed in the material of the plastic bag 22 and penetratable by a needle. Through said first plug 18 the plastic bags 22 can be filled with the medicament to be administered to the patient.

The plastic bags are also provided with a second plug 24 placed in the material thereof and which serves as a coupling piece towards the throttle means 16.

The liquid producing a vapour pressure and received by the bellows 12 exerts a pressure on the bags 22, said pressure being uniformly distributed by the liquid surrounding said bags. On opening the throttle means a clearly defined quantity of the medicament consequently passes out of the bags 22 and into the catheter and consequently into the body of the patient.

In the case of the presently proposed infusion pump construction the cleanness and sterility requirements with respect to the casing interior are far lower, because the medicament to be administered does not come into contact with the casing wall. In the preferred embodiment there is also no need for an absolute sealing of the casing, because the medicament is received by the bag and when a leak occurs in the bellows, the propellant is bound by the liquid surrounding the bag.

I claim:

1. Implantable infusion pump having a casing which receives a bellows containing a propellant producing a vapor pressure, which casing forms a space and is provided with a throttle means and a connection for a catheter characterized in that the space receives at least two bags made from a resilient plastic and containing a medicament, provided with a coupling piece, and connected to the throttle means.

2. Infusion pump according to claim 1, characterized in that the casing is made from plastic.

3. Infusion pump according to claim 1, characterized in that the upper surface of the casing directed towards the skin of the patient following implantation is provided with a number of recesses corresponding to the number of bags and which receive a plug penetrable by a needle.

4. Infusion pump according to claim 1, characterized in that the coupling piece is constructed as a plug placed in the material of the plastic bag.

5. Infusion pump according to claim 1, characterized in that the part of the space not occupied by the bag is filled with a liquid.

6. Infusion pump according to claim 1, characterized in that the liquid binds the propellant.

* * * * *